(12) United States Patent
Coffey

(10) Patent No.: US 9,554,945 B2
(45) Date of Patent: *Jan. 31, 2017

(54) COMBINATION SIS AND VACUUM BANDAGE AND METHOD

(71) Applicant: KCI Medical Resources, Grand Cayman (KY)

(72) Inventor: Arthur C. Coffey, Carmel, IN (US)

(73) Assignee: KCI Medical Resources Unlimited Company, Grand Cayman (KY)

( * ) Notice: Subject to any disclaimer, the term of this patent is extended or adjusted under 35 U.S.C. 154(b) by 0 days.

This patent is subject to a terminal disclaimer.

(21) Appl. No.: 14/984,932

(22) Filed: Dec. 30, 2015

(65) Prior Publication Data

US 2016/0106594 A1    Apr. 21, 2016

Related U.S. Application Data

(63) Continuation of application No. 14/272,291, filed on May 7, 2014, now Pat. No. 9,248,052, which is a
(Continued)

(51) Int. Cl.
*A61F 13/02*    (2006.01)
*A61L 15/32*    (2006.01)
(Continued)

(52) U.S. Cl.
CPC ..... *A61F 13/0216* (2013.01); *A61F 13/00012* (2013.01); *A61F 13/00068* (2013.01);
(Continued)

(58) Field of Classification Search
CPC .. A61F 13/0216; A61F 13/022; A61F 13/023; A61F 13/02; A61L 15/32; A61L 15/325; A61L 15/40
See application file for complete search history.

(56) References Cited

U.S. PATENT DOCUMENTS 1,355,846 A    10/1920  Rannells
2,547,758 A    4/1951   Kelling
(Continued)

FOREIGN PATENT DOCUMENTS

AU    550575 B2    3/1986
AU    745271 B2    3/2002
(Continued)

OTHER PUBLICATIONS

Louis C. Argenta, MD and Michael J. Morykwas, Phd; Vacuum-Assisted Closure: A New Method for Wound Control and Treatment: Clinical Experience; Annals of Plastic Surgery.
(Continued)

*Primary Examiner* — Lakshmi Channavajjala

(57) ABSTRACT

A wound care bandage for treating a wound is provided. The bandage includes an SIS layer to be placed on the wound surface and a cover to placed over the wound. The bandage further includes a structure to provide a vacuum space. A method for promoting wound healing is further provided. The method includes applying the above-mentioned wound care bandage to the wound and creating a vacuum in the vacuum space to draw blood controllably from the wound into the SIS layer.

20 Claims, 2 Drawing Sheets

Related U.S. Application Data continuation of application No. 11/242,543, filed on Oct. 3, 2005, now Pat. No. 8,747,887, which is a continuation of application No. 09/855,287, filed on May 15, 2001, now abandoned.

(60) Provisional application No. 60/206,226, filed on May 22, 2000.

(51) Int. Cl.
    *A61L 15/40*     (2006.01)
    *A61M 1/00*     (2006.01)
    *A61F 17/00*     (2006.01)
    *A61F 13/00*     (2006.01)
    *A61M 27/00*     (2006.01)

(52) U.S. Cl.
    CPC ............ *A61F 13/02* (2013.01); *A61F 13/022* (2013.01); *A61F 13/0226* (2013.01); *A61F 13/0253* (2013.01); *A61F 17/00* (2013.01); *A61L 15/32* (2013.01); *A61L 15/325* (2013.01); *A61L 15/40* (2013.01); *A61M 1/0088* (2013.01); *A61F 2013/0054* (2013.01); *A61F 2013/00174* (2013.01); *A61F 2013/00357* (2013.01); *A61F 2013/00536* (2013.01); *A61F 2013/00859* (2013.01); *A61F 2013/00927* (2013.01); *A61M 27/00* (2013.01)

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,970,298 A * | 11/1990 | Silver et al. ............ | A61K 9/70 128/DIG. 8 |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,695,823 B1 * | 2/2004 | Lina et al. ............ | A61F 13/0203 602/43 |
| 6,814,079 B2 | 11/2004 | Heaton et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |

(56) References Cited

FOREIGN PATENT DOCUMENTS

| | | |
|---|---|---|
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/10424 A1 | 9/1990 |
| WO | 93/09727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Jornal of Textile and Apprel, Technology and Management , vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery; Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment; Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Moyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.

* cited by examiner

COMBINATION SIS AND VACUUM BANDAGE AND METHOD

CROSS REFERENCE TO RELATED APPLICATIONS

This application is a continuation of U.S. patent application Ser. No. 14/272,291, filed May 7, 2014, which is a continuation of U.S. patent application Ser. No. 11/242,543, filed Oct. 3, 2005, now U.S. Pat. No. 8,747,887, which is a continuation of U.S. patent application Ser. No. 09/855,287, filed May 15, 2001, which claims the benefit of U.S. Provisional Application, Ser. No. 60/206,226, filed May 22, 2000, all of which are hereby expressly incorporated by reference herein.

BACKGROUND OF THE INVENTION

The present invention relates to wound care and more particularly to the provision of an SIS wound care cover used in combination with a vacuum bandage. The invention contemplates both apparatus and a method for using the apparatus.

It is known to use small intestine submucosa (SIS) in wound care treatment, particularly the application of layers of SIS directly upon an open wound that has been debrided and cleaned. SIS is described in the following U.S. Pat. Nos. 5,855,619, 5,866,414, 5,753,267, 5,762,966, 5,755,791, 4,902,508, 4,956,178, 5,275,826, 5,281,422, 4,352,463, 5,372,821, 5,445,833, 5,516,533, 5,573,784, 5,645,860, 5,641,518, 5,711,969, and 5,695,998. These patents are hereby incorporated herein by reference for purposes of disclosing the nature of SIS.

SIS has been described as a natural acellular biomaterial used to repair, support, and stabilize a wide variety of anatomical defects and traumatic injuries. See, for example, Cook® Online New Release provided by Cook Biotech at "www.cookgroup.com". The SIS material is a tissue engineered collagen matrix derived from porcine small intestinal submucosa that models the qualities of its host when implanted in human soft tissues. Further, it is taught that the SIS material provides a natural scaffold-like matrix with a three-dimensional structure and biochemical composition that attracts host cells and supports tissue remodeling. Surgisis™ Soft Tissue Repair Biomaterial and Oasis™ Wound Dressing Biomaterial are available for remodeling partial thickness skin injuries (Cook Biotech, Bloomington, Ind.). The Oasis™ Wound Dressing is provided in single thickness, fenestrated sheets. It will be appreciated that SIS is readily available for use as a wound dressing.

While small intestine submucosa is available, other sources of submucosa are known to be effective for tissue remodeling. These sources include, but are not limited to, stomach, bladder, alimentary, respiratory, or genital submucosa. See, e.g., U.S. Pat. Nos. 6,171,344, 6,099,567, and 5,554,389, hereby incorporated by reference. Further, it is known that these various submucosa materials may be derived from non-porcine sources, including bovine and ovine sources. Additionally, other collagen matrices are known, for example lamina propria and stratum *compactum*.

It is also known to use a vacuum treatment bandage for accelerating wound healing. A vacuum bandage is a bandage having a cover for sealing about the outer perimeter of the wound and under which a vacuum is established to act on the wound surface. This vacuum applied to the wound surface accelerates healing of chronic wounds. Typically, suction tubes are provided for drawing exudate away from the wound, and the suction tubes may be used to create the vacuum under the cover. If the cover is a flexible cover, which is typically more comfortable for the patient, a porous packing may be provided under the cover to provide the space in which the vacuum is formed. Additionally, it is known a heater within a wound treatment apparatus to promote healing. The following U.S. Pat. Nos. establish the nature of vacuum and/or heat treatment bandages and devices: U.S. Pat. Nos. 6,095,992, 6,080,189, 6,071,304, 5,645,081, 5,636,643, 5,358,494, 5,298,015, 4,969,880, 4,655,754, 4,569,674, 4,382,441, and 4,112,947. All of such references are incorporated herein by reference for purposes of disclosing the nature of such vacuum or heat treatment of wounds.

As shown, for example, in U.S. Pat. No. 5,645,081 (hereinafter the '081 patent), a method of treating tissue damage is provided by applying negative pressure to a wound. The negative pressure is provided in sufficient duration and magnitude to promote tissue migration in order to facilitate the closure of the wound. FIG. 1 of the '081 patent discloses an open cell polyester foam section covering the wound, a flexible hollow tube inserted into the foam section at one end and attached to a vacuum pump at another end, an adhesive sheet overlying the foam section, and tubing to adhere to the skin surrounding the wound in order to form a seal that allows the creation of a vacuum when the suction pump is operating. The '081 patent further teaches use of negative pressure between about 0.1 and 0.99 atmospheres, and that the pressure can be substantially continuous, wherein the pressure is relieved only to change the dressing on the wound. Alternatively, the '081 patent teaches use of a cyclic application of pressure in alternating periods of application and non-application. In a preferred embodiment, pressure is applied in 5 minute periods of application and non-application.

The following pending applications, assigned to the same assignee as the present application is licensed, are also specifically incorporated herein by reference: U.S. patent application Ser. No. 09/369,113 filed Aug. 5, 1999 and titled Wound Treatment Apparatus, now U.S. Pat. No. 6,458,109, U.S. patent application Ser. No. 09/725,352 filed Nov. 29, 2000 and titled Vacuum Therapy and Cleansing Dressing for Wounds, now U.S. Pat. No. 6,685,681, and U.S. patent application Ser. No. 09/725,666 filed Nov. 29, 2000 and titled Wound Treatment Apparatus, now U.S. Pat. No. 6,755,807.

Various of prior art references teach the value of the vacuum bandage or the provision of vacuum to the surface of a chronic wound. Several Russian language articles exist that establish the efficacy of vacuum therapy. Examples of such prior art articles, each of which discusses the use of application of vacuum to a wound to promote healing, are as follows: Vacuum therapy in the treatment of acute suppurative diseases of soft tissues and suppurative wound, Davydov, et al. Vestn. Khir., September 1988 ("the September 1988 article"); Pathenogenic mechanism of the effect of vacuum therapy on the course of the wound process, Davydov, et al. Khirurigiia, June 1990 ("the June 1990 article"); and Vacuum therapy in the treatment of suppurative lactation mastitis, Davydov, et al., Vestn. Khir., November 1986 ("the November 1986 article").

The Russian articles distinguish wound drainage from use of vacuum therapy for healing, and they report that vacuum therapy results in faster cleansing of the wound and more rapid detoxification than with the traditional incision-drainage method. The November 1986 article describes the vacuum therapy protocol as 0.8-1.0 atmosphere for 20 minutes at the time of surgery, and subsequent 1.5 to 3 hour treatments at a vacuum of 0.1 to 0.15 atmosphere, twice daily. These Russian articles teach that use of negative pressure accelerates healing. The Russian articles further teach using this vacuum method to decrease the number of microbes in the wound. The June 1990 article teaches that vacuum therapy provides a significant antibacterial effect. The June 1990 article describes the stepped up inflow of blood to the zone around the wound, which leads to an increase in the number of leukocytes reaching the focus of inflammation. Moreover, the Russian articles teach improvement of local blood circulation using vacuum therapy. The September 1988 article teaches improved inflow of blood into the wound zone, which intensifies the repair processes. The June 1990 article teaches that vacuum therapy promotes mobilization of blood plasma, intertissue fluid, and lymph into the wound. The June 1990 article reports that cellular and non-cellular elements of connective tissue appear twice as quickly in wounds treated with vacuum therapy. Subsequent articles and patents further develop the benefits obtained with vacuum therapy. The prior art, therefore, teaches the benefit and value of a vacuum bandage.

SUMMARY OF THE INVENTION

According to the present invention, a wound care bandage is provided that combines the advantages of SIS and vacuum therapy to control and enhance the flow of fluid from the wound bed and into the SIS material. The present invention, therefore, is a method for controllably drawing fluid from the surrounding tissue and into an SIS layer placed on the wound, thereby enhancing the healing and restructuring properties of the SIS.

The present invention comprises structure to provide a space above the SIS and the wound bed, in which space a vacuum is developed to cause blood flow from the wound bed into the SIS. Furthermore, the method contemplates controlling the vacuum level and the application time of the vacuum to present optimum blood flow from the wound bed into the SIS.

In preferred embodiments, the wound care bandage includes an SIS layer to be placed in contact with the wound bed. As mentioned above, the wound care bandage further includes a structure placed over the SIS layer to provide a vacuum space between the SIS layer and a cover placed over the structure and SIS layer. The cover is coupled to the patient's skin surrounding the wound to provide a sealed environment. A vacuum source is coupled to the wound covering for communication with the vacuum space created by the structure. The vacuum source is used to create a vacuum within the sealed environment in order to draw blood from the wound bed up through the SIS layer to promote the healing process. The vacuum suction is to be at a level sufficient to draw blood to the SIS layer, for example, 125 mm Hg. It will be appreciated, however, that varying levels of vacuum suction and varying protocols for the duration of application of vacuum are within the scope of the present invention.

In further embodiments, the space-providing structure is a porous or reticulated pad or other structure having air passageways extending from the SIS layer to the cover. In still further embodiments, the space-providing structure may be a foam ring, or it may be the cover itself, provided that the cover is sufficiently rigid.

Thus, in one aspect of this invention a wound care bandage is provided comprising a collagen matrix formed for placement on a wound, a cover configured for placement over the wound to provide a sealed environment around the wound and adapted for communication with a vacuum source, and a structure for placement between the collagen matrix and the cover and configured to provide a vacuum space. In preferred embodiments, the collagen matrix is a layer of submucosa.

In another aspect of this invention a wound care bandage is provided comprising an SIS layer adapted to be placed on a wound, and a cover configured to be placed over the wound and the SIS layer to provide a vacuum space between the SIS layer and an inside surface of the cover, the space being connectable with a vacuum source.

Still another aspect of this invention includes a method for promoting wound healing comprising the steps of providing a wound care bandage having an SIS layer adapted to be placed on a wound, a cover to be placed over the wound to provide a vacuum space above the wound, a structure to define the vacuum space between the SIS layer and the cover, and creating a vacuum within the vacuum space to controllably draw blood from the wound into the SIS layer placed over the wound.

Yet another aspect of this invention is directed to a method for promoting wound healing comprising the steps of applying an SIS layer to a wound surface, placing a support structure over the SIS layer, placing a cover over the wound, SIS layer and support structure to define a vacuum space, connecting the cover to a vacuum source, and creating a vacuum within the vacuum space.

An additional aspect of this invention is directed to a method for promoting wound healing comprising the steps of applying a collagen matrix to a wound surface, creating a vacuum space in communication with the wound and the collagen matrix, and generating a vacuum within the vacuum space in a magnitude and duration sufficient to draw blood from the wound into the collagen matrix.

A final aspect of this invention is a kit for promoting wound healing, the kit comprising a submucosa layer for contacting the wound, a porous pad, and a cover for creating a seal around the wound and configured for communication with a vacuum source.

BRIEF DESCRIPTION OF THE DRAWINGS

The detailed description particularly refers to the accompanying figures in which.

DETAILED DESCRIPTION OF THE DRAWINGS

Figure 1:
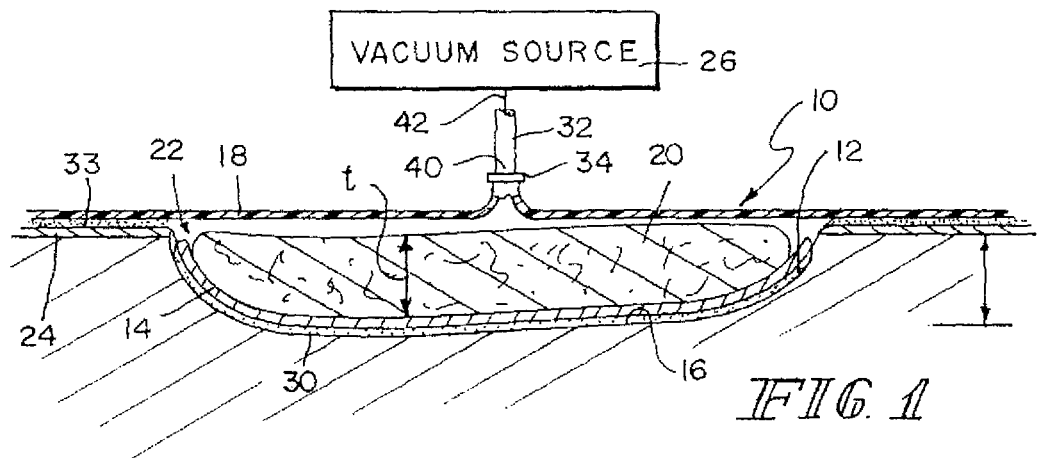
FIG. 1 is a sectional view of a debrided wound and a wound care bandage showing an SIS layer, a porous pad or filler, and a cover of the wound care bandage, and further showing the cover of the wound care bandage in communication with a tube adapted to lead to a vacuum source.
Figure 2:
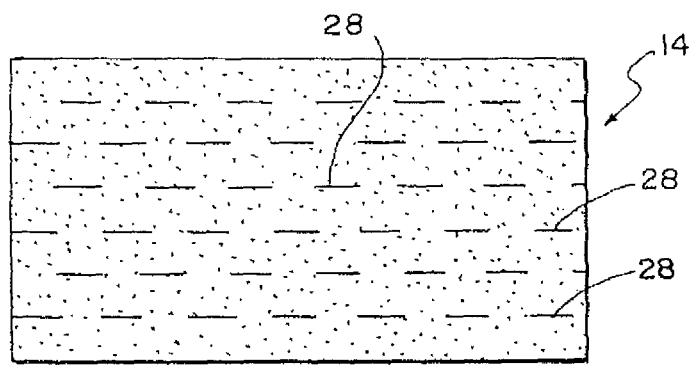
FIG. 2 is a plan view of the SIS layer shown in FIG. 1 showing fenestrations in the SIS layer.

A wound care bandage 10 is provided, as shown in FIGS. 1-5, for use with a debrided wound 12. Referring to FIG. 1, bandage 10 includes a small intestinal submucosa (SIS) layer 14 which lies adjacent to a wound surface 16 of wound 12. Bandage 10 further includes a cover 18 for placement over wound 12 and a structure 20, 120, 220, or 320 positioned between SIS layer 14 and cover 18 in order to create a vacuum space 22. Cover 18 is coupled to a portion of the patient's skin 24 surrounding wound 12 in order to enclose wound 12, SIS layer 14, and structure 20, 120, 220, or 320 within a sealed environment. Bandage 10 further includes a means for communicating vacuum space 22 with a vacuum source 26. The wound care bandage 10, therefore, combines the healing properties of the SIS layer 14 with the acceleration provided by the vacuum therapy.

SIS layer 14, which is applied directly to wound surface 16, may be fenestrated (or perforated) to prevent fluid accumulation below the SIS layer 14. Such fenestrations 28 are shown, for example, in FIG. 2. Equipment is available for fenestrating skin grafts and it is contemplated that such equipment could also be used to fenestrate SIS layer 14. These fenestrations 28, or perforations, in the SIS layer 14 permit blood from the wound 12 to migrate upwardly into the SIS layer 14 and deposit cells to start the tissue growth in the SIS framework of the SIS layer 14.

Further, SIS layer 14 may be formed to include one single sheet of SIS or multiple sheets of SIS. For SIS layer 14 including multiple SIS sheets, the sheets may be positioned in any number of orientations relative to each other. It is further within the scope of the disclosure for SIS layer 14 to have any reasonable thickness for its use in bandage 10. It is also known in the art that larger sheets of submucosa may be formed by fusing multiple strips of submucosa tissue. See U.S. Pat. No. 5,711,969, already incorporated by reference. In a preferred embodiment, SIS layer 14 is sized to fit the wound and is flexible in order to allow the SIS layer 14 to conform to any complex wound or wound surface. Additionally, it is known to treat wounds with SIS provided in fresh, frozen, or lyophilized forms. Lyophilized SIS may be used in the dried form, or it may be hydrated prior to use.

In some optional embodiments, a biological glue 30 is provided between the debrided wound surface 16 and the SIS layer 14 in order to hold the SIS layer 14 in a stationary position against the wound surface 16, as shown, for example, in FIG. 1. One type of biological glue 30 used may be a fibrin sealant, for example. It is within the scope of this disclosure, however, to include any type of biological glue sufficient for holding the SIS layer 14 stationary relative to wound surface 16.

SIS is intended to identify porcine small intestine submucosa. While reference is made herein to SIS, it will be appreciated that small intestine submucosa may be obtained from other animal sources, including cattle, sheep, and other warm-blooded mammals. Further, other sources of submucosa from various tissue are known to be effective for tissue remodeling as well. These sources include, but are not limited to, stomach, bladder, alimentary, respiratory, and genital submucosa. Such submucosa-derived matrices comprise highly conserved collagens, glycoproteins, proteoglycans, and glycosaminoglycans. Additionally, other collagen matrices are known that can act as a biological scaffolds. Thus, it is understood that while the preferred embodiment uses SIS, other collagen matrices may be used within the scope of this invention.

The structure of bandage 10, is provided to form vacuum space 22 between SIS layer 14 and cover 18. A structure supports cover 18 while providing air passageways to the wound surface 16 and the SIS layer 14. As shown in FIG. 1, the structure is preferably a reticulated or porous filler or pad 20 having airflow passageways (not shown) extending throughout pad 20. It is preferred that pad 20 be rather flexible to conform to any complex wound or wound surface and to be comfortable for the patient. Further, it is preferred that the thickness of the structure is selected to provide proper vacuum access to all parts of the wound to be served. It is further preferred that a thickness, t, of the reticulated flexible pad 20 be approximately one to two centimeters. The reticulated or porous pad 20 may be cut by the surgeon to be larger than the SIS layer 14 and even larger than the wound 12.

Figure 3:
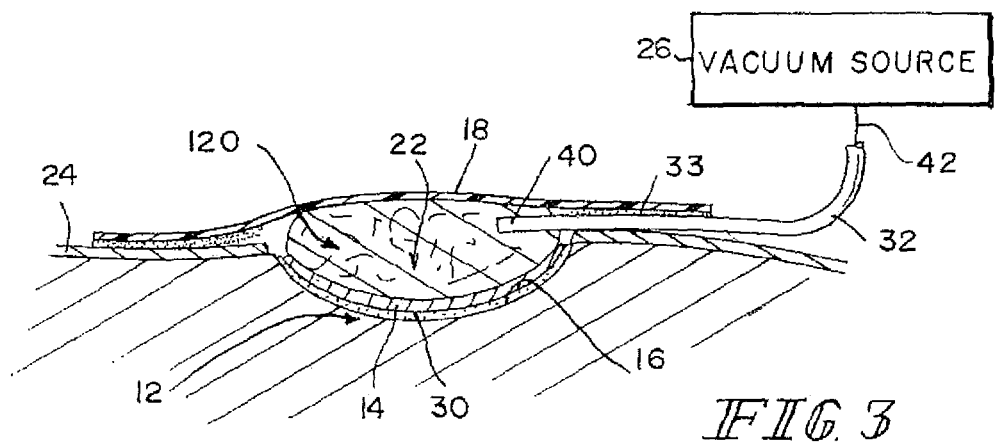
FIG. 3 is a sectional view of another debrided wound and another wound care bandage including an SIS layer, a walled structure to provide a vacuum space, a covering, and a vacuum tube positioned to lie under the cover and in communication with the vacuum space at one end and a vacuum source an another end.
Figure 4:
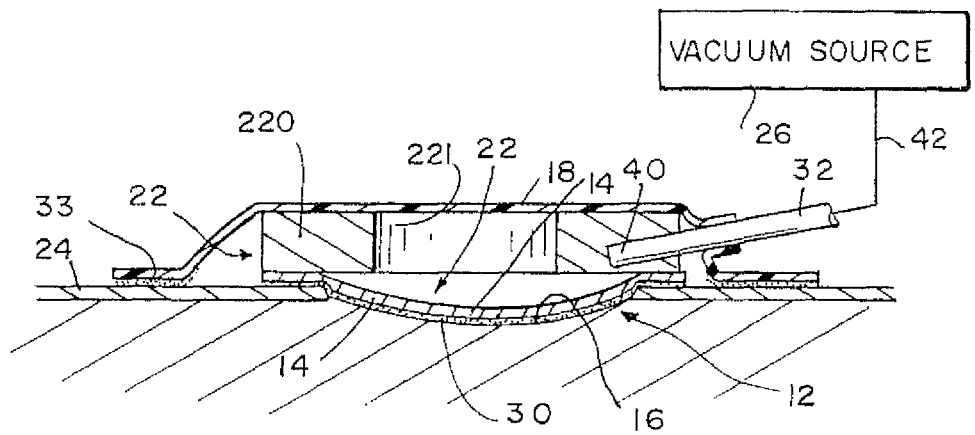
FIG. 4 is a sectional view of another embodiment of the present invention showing another wound care bandage over a debrided wound and showing the bandage including an SIS layer, a ring-shaped structure defining a vacuum space in communication with the vacuum source, and a cover positioned over the structure.

Although porous pad 20 has been described above, it is within the scope of this disclosure to include any such structure which functions to create a space between the SIS layer 14 and the cover 18 and permits air flow from the wound 12 to transmit negative pressure to the wound surface 16. As shown in FIG. 3, the structure 120 may be gauze, or, as shown in FIG. 4, the structure may be a foam ring 220 or other such ring to position cover 18 in spaced-apart relation to SIS layer 14. Ring 220 includes an aperture defined by an inner wall 221 of the ring 220. The vacuum space 22 is thus defined by the SIS layer 14, the cover 18, and the inner wall 221 of ring 220.

Figure 5:
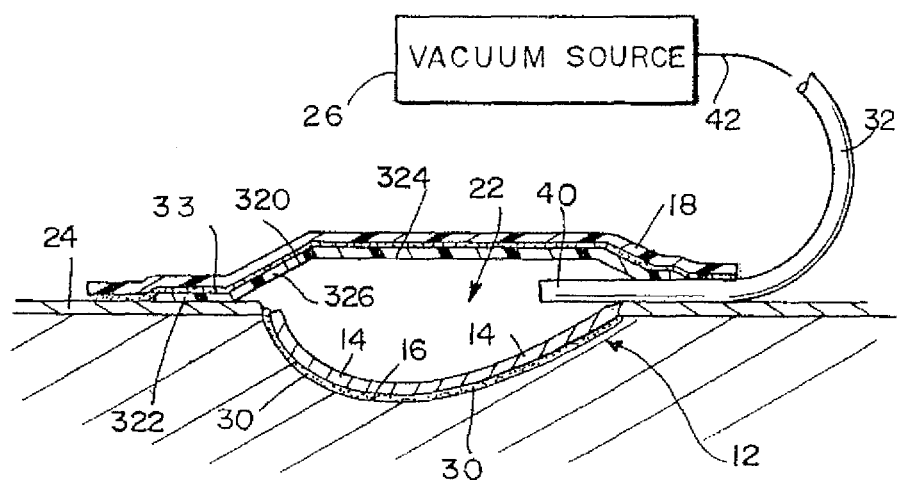
FIG. 5 is a sectional view of another embodiment of the present invention showing the bandage including a semi-rigid walled structure for defining a vacuum space in communication with the vacuum source.

Further, as shown in FIG. 5, for example, the structure may be a rigid dome or a preferably semi-rigid dome 320 which supports the cover 18 above the SIS layer 14. Semi-rigid dome 320 includes a lower member 322 adapted to lie adjacent the patient's skin surrounding wound 12, an upper member 324 normally spaced-apart from SIS layer 14, and a middle member 326 for supporting the upper member 324 in spaced-apart relationship with the SIS layer 14. Semi-rigid dome 320 may be generally dome-shaped, for example, as well. Although such examples as porous pad 20, foam ring 220, and semi-rigid dome 320 have been provided as examples for the structure, it is within the scope of this disclosure for bandage 10 to include any space providing structure above the SIS layer 14 and below the cover 18 for communication with a vacuum service 26.

Cover 18 of the bandage 10 lies over the space-providing structure to fully enclose the structure, SIS layer 14, and wound 12. Cover 18 is coupled to the patient's skin 24 which surrounds the wound 12. For example, cover 18 may be a thin transparent, non-porous adhesive sheet to adhere to the surface of the skin 24 about the wound 12 to provide a vacuum enclosure. An adhesive 33 for coupling cover 18 to skin 24 is shown in FIGS. 1 and 3-5. A product such as Tegaderm™ (3 M Health Care Ltd., (St. Paul, Minn.)) would be suitable for the cover, for example. It is within the scope of this disclosure, however, to include any suitable non-porous impermeable or semi-permeable sheet. While a flexible or semi-rigid sheet is preferred for patient comfort, a rigid cover, such as a glass dome, is within the scope of this invention. When a rigid cover is used, a separate space-providing structure is not needed, as the rigid cover may be configured to provide the vacuum space.

In order to encourage blood flow to the wound 12 and wound surface 16, vacuum space 22 of wound care bandage 10 is connected with vacuum source 26. A vacuum tube 32 may be provided, for example, for fluid communication with vacuum space 22 and vacuum source 26. As shown in FIG. 1, vacuum tube 32 is coupled to cover 18 and in communication with vacuum space 22. A first end 40 of tube 32 includes a collar 34 coupled to an aperture of the cover 18. As shown diagrammatically, a second end 42 of tube 32 is coupled to vacuum source 26.

In other embodiments, as shown in FIGS. 3-5, for example, tube 32 is placed under cover 18 and into vacuum space 22. Cover 18 is sealed around tube 32 in order create a sealed environment for the vacuum to function properly. The vacuum may be provided by a suction tube disposed in the space and configured to draw excess wound drainage away from the wound. Another type of fluid connection system between a wound dressing and a vacuum source is disclosed in U.S. Pat. No. 4,969,880, incorporated herein by reference. Furthermore, while first end 40 of tube 32 is shown in FIGS. 3 and 4 as being located in the structure 120 or 220, it is understood that first end 32 may be placed directly on the SIS layer 14. Additionally, it is understood that tube 32 may be a Jackson-Pratt type drain, with holes distributed along its length adjacent first end 32.

The vacuum may be provided in vacuum space 22 for controlled periods of time. For example, initially, the vacuum may be applied for a sufficient time to draw blood into the SIS layer 14, such as up to 125 mm Hg, for example. It will be appreciated that this invention contemplates developing different protocols for amounts of vacuum and application times. It will also be appreciated that the vacuum may be provided by a perforated tube positioned and configured to carry away excess wound drainage.

In treating wound 12, a caretaker first cleans and prepares the wound surface 16. Once wound surface 16 is prepared, bandage 10 is to be applied to the wound. SIS layer 14 is positioned over the wound 12 to cover the prepared wound surface 16. Structure 20, 120, 220, or 320 is placed over the SIS layer 14 to define the vacuum space and cover 18 is placed over the wound 12, SIS layer 14, and structure 20. Cover 18 is connected to a vacuum source 26. Finally, suction is applied to the vacuum space 22 in sufficient magnitude and duration to draw blood from the wound into the SIS layer 14. Optionally, a biological glue 30 may be placed on the wound surface 16 prior to application of the bandage 10.

Vacuum may be applied at any magnitude or duration to promote inflow of blood from the wound into the layer of SIS. Preferably, vacuum may be applied from 0.1 to 0.99 atmospheres, and more preferably 0.1 to 0.15 atmospheres. In one embodiment, vacuum is applied essentially continuously until healing takes place. In another embodiment, vacuum is used in periods of application and non-application, and the structure and cover may be removed during periods of non-application. These alternating periods may include one or two periods of application each day for several days. In another embodiment, the negative pressure is applied in 5 minute periods of application and non-application.

It is known that SIS can be integrated into the wound and restructured to resemble the surrounding tissue. Thus, while the magnitude and duration of application of vacuum may vary, in a preferred embodiment the SIS remains on the surface of the wound for the duration of treatment. In optional embodiments, additional layers of SIS may be added as the SIS is integrated into the wound. The additional layers may be smaller pieces to be placed on localized areas of integration, or, because the vacuum promotes blood flow into the SIS layer, may be full size pieces conforming to the size of the wound surface.

Thus, in one embodiment the present invention is a method for treating wounds comprising the steps of preparing the wound surface, applying a bandage to the wound, the bandage having an SIS layer secured over the wound and a cover above the wound and the SIS layer to define a vacuum space between the SIS layer and the cover, and applying suction to the vacuum space to draw blood from the wound into the SIS layer.

Although this invention has been described in detail with reference to certain embodiments, variations and modifications exist within the scope and spirit of the invention as described and defined in the following claims.

The invention claimed is:

1. A wound care bandage for use with a vacuum source, the wound care bandage comprising:
   a collagen matrix configured to be placed on a wound of a patient for integration into the wound;
   a support structure configured for placement over the collagen matrix to provide a vacuum space defined by the support structure and the collagen matrix and adapted to receive negative pressure from the vacuum source;
   a cover configured to be disposed over the support structure and the wound to provide a sealed environment for the vacuum space over the wound; and
   wherein the support structure comprises a lower member adapted to be disposed adjacent skin surrounding the wound without sutures or staples when negative pressure is applied to the vacuum space, an upper member, and a middle member between the lower member and the upper member, and wherein the support structure is sufficiently rigid to maintain a spaced-apart relationship with the collagen matrix when negative pressure is applied to the vacuum space.

2. The bandage of claim 1, wherein the middle member is sufficiently rigid to support the upper member in the spaced-apart relationship when negative pressure is applied to the vacuum space.

3. The bandage of claim 2, wherein the middle member includes an inner wall that defines the vacuum space with the collagen matrix and the upper member.

4. The bandage of claim 1, wherein the upper member is sufficiently rigid to maintain the spaced-apart relationship when negative pressure is applied to the vacuum space.

5. The bandage of claim 4, wherein the middle member includes an inner wall that defines the vacuum space with the collagen matrix and the upper member.

6. The bandage of claim 1, wherein the collagen matrix comprises a submucosa layer.

7. The bandage of claim 1, wherein the bandage further includes a biological glue for positioning between the wound and the collagen matrix for holding the collagen matrix stationary relative to the wound.

8. The bandage of claim 7, wherein the glue is a fibrin sealant.

9. The bandage of claim 1, wherein the cover includes a first surface and a second surface and the first surface includes an adhesive for adhering to skin adjacent the wound.

10. The bandage of claim 1, wherein the support member includes air passageways between the cover and the collagen matrix to further define the vacuum space.

11. The wound care bandage of claim 1, wherein the collagen matrix is a sheet of collagen matrix material having a three-dimensional structure configured to support tissue remodeling when positioned on the wound.

12. The wound care bandage of claim 11, wherein the collagen matrix is selected from the group consisting of submucosa, lamina propria, and stratum compactum.

13. The wound care bandage of claim 11, wherein the upper member is sufficiently rigid to maintain the spaced-apart relation when negative pressure is applied to the vacuum space.

14. A method for promoting wound healing using a vacuum source, the method comprising:
applying a collagen matrix to a wound surface;
positioning a support structure having a lower member adapted to be disposed adjacent skin surrounding the wound, an upper member matter, and a middle member between the lower member and the upper member;
placing a cover over the wound and the support structure to create a vacuum space defined by the collagen matrix, the cover, the middle member, and the upper member, wherein the support structure is sufficiently rigid to maintain a spaced-apart relationship with the collagen matrix when negative pressure is applied to the vacuum space; and
providing a vacuum to the vacuum space from the vacuum source in a magnitude over a period of time sufficient to hold the upper member in place without sutures or staples and facilitate integration of the collagen matrix into the wound surface with the support structure being removable from the wound after integration of the collagen matrix into the wound.

15. The method of claim 14, wherein the first collagen matrix comprises a submucosa layer.

16. The method of claim 14, wherein the support structure includes air passageways between the cover and the collagen matrix to further define the vacuum space.

17. The method of claim 14, wherein the middle member is sufficiently rigid to support the upper member in the spaced-apart relation when negative pressure is applied to the vacuum space.

18. The method of claim 17, wherein the middle member includes an inner wall that defines the vacuum space along with the collagen matrix and the upper member.

19. The method of claim 14, wherein the vacuum is applied intermittently by cycling the vacuum source on and off at intervals over the duration period to controllably draw fluid from the wound into the collagen matrix.

20. The method of claim 14, wherein the vacuum is applied by turning the vacuum source on at a constant rate and turning the vacuum source off after the duration period to controllably draw blood from the wound into the collagen matrix.

* * * * *